United States Patent [19]
Duffy et al.

[11] Patent Number: 5,885,784
[45] Date of Patent: Mar. 23, 1999

[54] PROCESS FOR MAKING TRIGLYCERIDE CONTROLS, CALIBRATORS AND STANDARDS COMPRISING NOVEL TRIGLYCERIDE SUBSTITUTES

[75] Inventors: Thomas H. Duffy, Santa Ana; Carter J. Grandjean, Norco; Roy F. Schall, Jr., Glendora, all of Calif.

[73] Assignee: Bio-Rad Laboratories, Inc., Hercules, Calif.

[21] Appl. No.: 584,906

[22] Filed: Jan. 11, 1996

Related U.S. Application Data

[63] Continuation-in-part of Ser. No. 298,816, Aug. 31, 1994, abandoned.

[51] Int. Cl.⁶ .................................................. C12Q 1/60
[52] U.S. Cl. .............................. 435/18; 435/11; 436/13; 436/16
[58] Field of Search .............................. 435/11, 198, 18; 436/13, 16, 18, 71

[56] References Cited

U.S. PATENT DOCUMENTS

| | | | |
|---|---|---|---|
| 3,955,925 | 5/1976 | Prosch ........................................ | 436/13 |
| 4,011,045 | 3/1977 | Bonderman .......................... | 23/230 B |
| 4,701,417 | 10/1987 | Portenhauser et al. .................... | 436/13 |
| 4,816,411 | 3/1989 | Yun et al. ................................. | 436/13 |

FOREIGN PATENT DOCUMENTS

0140495A1   8/1984   European Pat. Off. .

OTHER PUBLICATIONS

Erlanson, C., *Tributyrine As a Substrate For . . .* Scand T. Gastru 5: 293–295 (1970).
Henry, J., *Clinical Diagnosis and Management by Laboratory Methods*, 16th ed., W.B. Saunders Co., Philadelphia, PA. 1979: 190–1, 203–4, 753–4.
Kurooka S., *Properties of Serum Lipase in Patents . . .* T. Biochem 84, 1459–1466 (1978).
Pesce, A.J., Kaplan, L.A., Editors, *Methods in Clinical Chemistry*, C.V. Mosby Co., St. Louis, MO 1987: 848–853, 1215–1227.
Tietz, N. Editor, *Textbook of Clinical Chemistry*, W. B. Saunders Co., Philadelphia PA 1986: 735–740.
Tietz, N.W. et al., 1993, Clin. Chem. 39/5: 746–756.
Witter, R.F., Whitner, V.S., "Determination of Serum Triglycerides", in Nelson, G.J., Editor, *Blood Lipids and Lipoproteins: Quantitation Composition and Metabolism*, Wiley Interscience, New York NY 1972: 75–111.
Klotzsch, S., "Practical Limitations in the Measurement of Triglycerides", Pentext, Fall, 1992, a publication of Miles, Inc., Tarrytown, NY: 1–4.
The Merck Index 11th Ed. Budauari Ed., Merck and Co. Ranway N.J. 1989, #9644.
Tietz N., Textbook of Clinical Chemistry, Saunders Co. Philadelphia, pp. 735–740, 1986.
Pesce A., Methods in Clinical Chemistry, Mosby Co. Washington DC, pp. 848–853, 1215–1227, 1987.

*Primary Examiner*—Ralph Gitomer
*Attorney, Agent, or Firm*—Arthur S. Morgenstern; Robert P. Blackburn

[57] ABSTRACT

Materials and compositions for making triglyceride controls, calibrators and standards are described. The materials are mono- and di- and tri- glycerides of medium length fatty acids mixed into compositions of human serum or other protein solutions to form stable, miscible solutions suitable for use as controls, calibrators and standards in clinical chemistry for measurement and quality control in assays for triglycerides. The materials described have been used as vehicles for oil-soluble, water-insoluble pharmaceuticals and as facial emollient oils for cosmetics, and as such are safe, functional, stable, rancid-resistant and very inexpensive compared with pure materials synthesized or described previously.

14 Claims, No Drawings

PROCESS FOR MAKING TRIGLYCERIDE CONTROLS, CALIBRATORS AND STANDARDS COMPRISING NOVEL TRIGLYCERIDE SUBSTITUTES

This is a continuation-in-part of application Ser. No. 08/298,816 filed on Aug. 31, 1994, now abandoned.

BACKGROUND OF THE INVENTION

The measurement of triglycerides in clinical chemistry is important as an indicator of the presence of pancreatic disease, hyperlipidemia, coronary artery occlusive disease, etc. In the clinical laboratory, in order to have confidence in these measurements a quality control system needs to be in place. Controls, calibrators, and standards are integral components of this quality control system and well known to those in the clinical chemistry field ( see pg 430, Textbook of Clinical Chemistry, by N. W. Tietz, W. B. Saunders Co., 1986). There is considerable literature on the use of triglycerides for controls, calibrators, and standards. These triglycerides include those extracted from egg yolk, purified olive oil (triolein) or others isolated from animal or human blood. However, there are inherent difficulties in using these materials in multiconstituent controls, calibrators or standards such as:

1. They are unstable to freeze-thaw processing.
2. They can precipitate, and this precipitation can concomitantly affect other analytes such as calcium and phosphate.
3. They tend to become easily and quickly contaminated by microbes, such contamination adversely affecting the products in which they are used.
4. They are usually poorly characterized mixtures causing reproducibility problems.
5. Their assayed values are not stable and continue to rise over time.
6. Some are too insoluble in protein solutions to be useful (controls, calibrators, or standards commonly contain triglyceride levels as high as 400 mg/dl).

Some clinical chemistry control manufacturers attempt to circumvent these difficulties by substituting glycerol for the triglyceride to mimic the chemistry of the true triglyceride. This approach has met with limited success because the hydrolysis step which is essential in certain assays is eliminated, and, for some assays requiring measurement of hydrolyzed fatty acids, glycerol is totally unsuitable.

Manufacturers could theoretically use synthetic triglyceride analogs such as, 2,3-dimercaptopropan-1-ol tributyrate, beta-naphthyl laurate, beta-naphthyl myristate, phenyl laurate and sorbitan esters, methylumbelliferone- and N-methylindoxyl myristate as components in controls, calibrators, or standards, but these materials are vastly too expensive and/or insoluble in a protein matrix to be practically useful. Normally, aqueous insoluble triglycerides are insufficiently soluble to be practically used in clinical controls. They can sometimes be made soluble by the use of a surfactant, but the surfactant often adversely affects other constituents, e.g. enzymes.

This invention relates to the new and innovative use of existing material as substitutes for human, animal or egg yolk triglycerides in multiconstituent clinical chemistry controls, calibrators, standards and related preparations. The substitute materials include medium carbon length (e.g. $C_8$, $C_{10}$, $C_{18}$) fatty acids esterified to glycerol to form mono- and di-glyceride mixtures, which are currently commercially used as vehicles for water-insoluble, oil-soluble pharmaceuticals and as emollient oils for facial creams and cosmetics. They are sufficiently soluble in protein solutions and yield stable triglyceride measurements on standing, without extraneous additional stabilizers required in other preparations. Similar materials which can also be used include, but are not limited to, glycerol tripropionate, and glyceryl tributrate. The use of these materials has avoided the problems of freeze-thaw instability, precipitation, microbial contamination, and poor characterization (and hence reproducibility) which are encountered with the previous materials. These new materials also are much less expensive to use than the previous materials and methods, thus making them practical for use in the manufacture of the multiconstituent clinical control materials. The invention covers not only the identification of the material but also techniques for its use.

SUMMARY OF THE INVENTION

Triglyceride substitutes (pseudotriglycerides or PSTG) have been identified for use in clinical chemistry controls, calibrators, standards and related preparations. The substitute materials are mixtures of medium carbon length ($C_3$–$C_{18}$) fatty acids esterified to glycerol that are relatively inexpensive, making them useful for the control materials. In addition, single components used in different chemistry areas, were found to be usable in the instant application without the need for emulsifiers. This invention also relates to the process of using the substitute materials.

DETAILED DESCRIPTION OF THE INVENTION

This invention deals with the identification of novel sources of PSTG's for use in multiconstituent clinical chemistry controls, calibrators, standards and related preparations (together referred to as control materials) . This invention also relates to the use of the substitute materials. The preferred PSTG's were found to be those that were inexpensive, soluble in a protein solution, chemically characterized, (and as a result reproducible) and stable making them practical for usage in manufacturing the commercial control materials. These PSTG's are also safe to handle. These materials were generally mixtures, rather than pure, single component items.

PSTG's were analyzed in protein based matrices to determine performance characteristics, as shown in examples hereafter. To analyze the solutions, commercially available clinical analyzers were utilized e.g., Ektachem (manufactured by Kodak), Dimension D-380 (from DuPont), Express (from Ciba Coming), and ACA (from DuPont) to read serum triglyceride levels. Procedures involve the specific measurement of glycerol after the hydrolysis of the fatty acid-containing moieties. The substitutes included Capmul MCM and Capmul MCM-90 (trademarks of Karlshamns Inc. for mixtures of mono- and di-glycerides of capylate and caprate), 1-mondecanoyl-rac-glycerol, glycerol tributyrate (tributyrin), glycerol tripropionate (tripropionate), monocaproyloyl glycerol (Sigma Chemical Co.) and monoglyceride of linoleic acid (e.g., Myverol from Eastman Chemical Co.). The above is a representative but not exhaustive list of the possible substitutes. It has been found that the solubility of these compounds is affected not only by the number of glycerol substituents, but also by the chain length of each substituent. For example, if all three hydroxyl groups on glycerol are esterified with fatty acids of chain lengths of less than 6 carbons (e.g. triproprionate or tributyrin) then the compounds are sufficiently soluble in an aqueous protein solution to be useful. However, the solubility of glycerides of substituents exceeding 6 carbons ($C_6$) in length become sufficiently insoluble as to be rendered useless without addition of emulsifying agents (surfactants). If only one hydroxyl group is esterified, leaving two hydroxyl groups to help solubility, glycerides with substituent fatty acid chains as long as $C_{18}$ can be used.

As indicated above, the materials used herein are frequently mixtures. For example, Capmul MCM is a mixture of $\geq 80\%$ monoglyceride and $\leq 20\%$ diglyceride. The fatty acid composition thereof is a further unspecified mixture of caprylic and capric acids esterified to glycerol to form the above glyceride composition. It contains <1% free fatty acid and <1% free glycerol. Capmul MCM-90 is a mixture of the following composition: $\geq 90\%$ monoglyceride and $\leq 10\%$ diglyceride. The fatty acid composition thereof is a further unspecified mixture of caprylic and capric acids esterified to glycerol to form the above glyceride composition. It contains <1% free fatty acid and <1% free glycerol.

The control being used in the assay could contain solely PSTG in an aqueous protein solution and, thus, function only as a control for triglyceride. In addition to the triglyceride component the control may contain components to control other assays (e.g. glucose and enzymes), preservatives, buffers, etc. and, thus, function as a multi-constituent control.

Triglyceride levels in normal fasting human serum range from 44–210 mg/dL. To determine if normal and abnormal triglyceride levels could be simulated by use of the substitute materials, serial dilutions were prepared from a concentrated solution of Capmul MCM in human serum (See Example 3). The results of these tests showed the linearity and quantitative recovery of PSTG in a human serum base. (See Example 3.) This quantitative recovery does not appear to be time dependent (See Example 1).

In addition, further work was done to determine that quantitative recoveries of PSTG are consistent over the majority of clinical analyzers and over a range of PSTG materials (See Examples 4–7).

To be useful in clinical materials, minimal stability criteria must be met, e.g. after 14 days refrigerated storage (2°–8° C.), a recovery of plus or minus 10% should be obtained when the PSTG is spiked into a protein base at normal or abnormal levels. The results of stability studies indicated these PSTG's would be commercially useful as controls, calibrators or standards (See Example 2). Also, to be useful, samples must be linear upon dilution, since high concentration human clinical samples are diluted to get within the assayed concentration range for the test. (Example 3.)

Once quantitative recovery and adequate stability was shown for the PSTG when spiked into a protein base, the material was utilized in a number of applications where triglycerides isolated from egg yolk or human or animal blood had been used by other laboratories, namely, to develop materials which could be used as controls for clinical assays for the quantitative and qualitative measurement of triglyceride in human serum (See Examples 4 and 8). These materials are usable not only in human serum, but also in matrices composed of serum from other animals, human or animal albumin or mixtures thereof, urine, spinal fluid, saliva, or other fluids containing protein, or mixtures of any of the aforementioned fluids.

The above describes the best mode contemplated by the inventors for the use of the PSTG materials. However, it is contemplated that the PSTG's could be used in place of triglyceride isolated from egg yolk, or isolated from animal or human blood, in all analytical procedures including, without limitation, radioimmunoassay, ELISA, and other analytical techniques. For example, most immunoassays, for the identification of an antigen, utilize either a labelled antigen or a labelled antibody. PSTG antigen or antibody could be labelled using various established techniques, for example, the addition of a radioactive label, an enzymatic label, a fluorescent label, a chemiluminescent label or other labels which would make the material useful in an immunochemical analytical technique. The label would serve as the reporting groups in the immunoassays. It is also contemplated that PSTG's might be purified and utilized, or perhaps even utilized without purification, in other analytical techniques where triglycerides isolated from egg yolk, or isolated from animal or human blood, might currently be used.

It is further contemplated that the PSTG's could be used as immunogens to develop an antibody. Polyclonal, monoclonal or other antibodies could be raised against the triglyceride substitutes. The technology for production of antibodies (polyclonal or monoclonal) has been well established. (See, for example, *Immunology*, Second Edition, I. Roitt et al, Gower Medical Publishing, London, 1989, page 82.)

Either the PSTG's or antibody produced therefrom could be immobilized on a solid support. Numerous supports could be used, for example agarose resins (Sepharose etc.), glass beads, etc. An immobilized antibody to triglyceride could act as a rapid and efficient purification tool to obtain pure triglyceride from crude sources. Likewise, pure antibody could be obtained utilizing immobilized PSTG material. These immunoaffinity chromatographic methods are well established in the literature. The preceding illustrates how immobilized ligands can be utilized but should not be construed to limit their usefulness. For example, immobilized triglyceride substitute antibody could be used as a stripping agent to obtain triglyceride free serum.

The following examples describe aspects of the stability and usefulness in various instruments of the PSTG. These materials and the products produced therefrom are also useful in manual techniques. (For a general discussion of procedures for triglyceride, see, for example, "Methods in Clinical Chemistry", A. J. Pesce et al, C. V. Mosby Co., St. Louis, 1987, Chap. 18, pp. 1215–1227.) However, these examples are not intended to limit the usefulness of the PSTG's or techniques for utilization thereof.

EXAMPLE 1

Effect of Time Upon Dissolution:

Using human serum as the matrix of choice, 7.5 mg of PSTG from Karlshamn (Capmul® MCM, lot # 30418-6) was added to 30 mL of serum in a glass bottle, and mixed by tumbling at room temperature. The concentration of Capmul added was 25 mg/dL. No additional solubilizing agents were used. Samples of the solution were periodically taken and assayed for triglyceride concentration using a lipase-containing assay specific for triglyceride on a Ciba Coming Express 550 Clinical Chemistry Analyzer. The following table shows that the material yields a triglyceride concentration with the Express analyzer, that dissolution is complete by 94 minutes and that the concentrations measured remain stable with time. Also, the measured concentration on the Express 550 was 212% of the amount added, demonstrating that PSTG reacts as if it were more potent than endogenous triglyceride. (The variation in the data for concentrations is caused by imprecision of the method of measurement and is well within the precision expected from the Express 550.)

TABLE 1

| Time (minutes) | Triglyceride concentration (mg/dL) | Net PSTG Added (mg/dL) |
|---|---|---|
| Endogenous Triglycerides (baseline) | 138 | 0 |
| 0 | 191 | 53 |
| 94 | 194 | 56 |
| 331 | 187 | 49 |
| 1424 | 189 | 51 |

EXAMPLE 2

Effect of Time and Temperature on PSTG Activity:

Similar to Example 1 above, 15 mg of PSTG was added to 30 mL of human serum in amber bottles. The solutions were assayed for triglyceride concentration on the Express 550, and separate samples were placed at 5° C., 23° C. and 30° C. The samples were assayed for triglyceride concentration at intervals for up to 12 days. The following table shows the results. All of the concentrations are in mg/dL. The data show that the control materials stored at 5° C. are stable for approximately 3 years, based on extrapolation of the accelerated 30° storage stability studies shown below.

TABLE 2

| Time | Storage @ 5° C. | | Storage @ 23° C. | | Storage @ 30° C. | |
|---|---|---|---|---|---|---|
| (days) | Control | PSTG | Control | PSTG | Control | PSTG |
| 0 | 140 | 245 | 135 | 243 | 131 | 248 |
| 0.25 | 128 | 241 | 128 | 243 | 131 | 251 |
| 0.50 | 128 | 241 | 128 | 242 | 131 | 243 |
| 2 | 128 | 243 | 132 | 241 | 135 | 248 |
| 4 | 135 | 245 | 137 | 253 | 143 | 267 |
| 6 | 136 | 250 | 143 | 262 | 152 | 272 |
| 11 | 145 | 256 | 159 | 282 | 176 | 301 |
| 12 | 172 | 282 | 191 | 300 | 206 | 322 |

EXAMPLE 3

The Effect of Concentration on PSTG Activity:

To 30 mL of human serum was added 32 mg of PSTG. The mixture was rotated for 60 hours at 5° C., after which aliquots were taken and further diluted with human serum. The triglyceride activity of the final solutions was determined on a DuPont ACA III Clinical Analyzer. The following table presents the data obtained. Units of concentration are mg/dL.

TABLE 3

| Serum Dilution | Total Conc. ACA | Baseline Conc. | PSTG Net Conc. | PSTG Calc. Conc. | Ratio |
|---|---|---|---|---|---|
| undiluted | 436 | 130 | 306 | 106.7 | 2.86 |
| 1:2 | 284 | 130 | 154 | 53.3 | 2.89 |
| 1:3 | 234 | 130 | 104 | 35.6 | 2.92 |
| 1:4 | 211 | 130 | 81 | 26.7 | 3.04 |
| 1:5 | 198 | 130 | 68 | 21.3 | 3.18 |
| 1:6 | 181 | 130 | 51 | 17.8 | 2.87 |

In this table the baseline concentration is the triglyceride activity due to endogenous material in the human serum, and the PSTG calculated concentration is the actual concentration based on the amount of PSTG that was weighed out. It is clear from this table that throughout the concentrations evaluated, the ratio, which is the total concentration minus the baseline concentration divided by the calculated concentration, remains fairly constant at about 2.9. This ratio may be different depending on the analyzer doing the measurement, or the specific PSTG used, but it still remains constant.

That the recovery of measured triglyceride using PSTG is quantitative and reproduceable is shown in Table 3 of Example 3 by the calculation of a ratio which remains constant, at about 2.9. This ratio will likely be different depending upon which PSTG is selected for use, but. for each PSTG, some fixed ratio will be obtained. This then permits the PSTG to be used as a standard or calibration material as well as a control. A calibrator or standard would be prepared as follows: to achieve a calibration value of 200 mg/dL, add to one liter of serum stripped of endogenous triglycerides 689.7 mg of PSTG (specifically in this case Capmul MCM). The calculation is as follows:

$$689.7 \text{ mg/L} \times 2.9 \times 0.1 \text{ L/dL} = 200 \text{ mg/dL}$$

To achieve other calibrator values, use proportionately more or less PSTG per liter of stripped serum. For other PSTG's aside from Capmul MCM, or other analytical procedures, the appropriate factor would be used to achieve the desired concentration of "triglyceride".

EXAMPLE 4

PSTG Activity as Measured on the Dupont D-380 Analyzer:

When various types of PSTG are added to a final concentration of 210 mg/dL in human serum, which has an endogenous triglyceride value of about 90 mg/dL, and is mixed for 6 hours at 5° C., they yield stable PSTG values. A sample of these solutions is then stored at 5° C., and assayed for triglyceride activity over time. The following table shows the data for these PSTG's when analyzed on a Dupont D-380 Analyzer.

TABLE 4

| | Brands of PSTG | | | | |
|---|---|---|---|---|---|
| Time (days) | Control | Myverol | Tripro | Capmul | Mono C-8 | Tribut |
| 0 | 86 | 237 | 248 | 228 | 256 | 234 |
| 2 | 95 | 230 | 265 | 216 | 245 | 222 |
| 5 | 95 | 234 | 289 | 221 | 242 | 225 |
| 9 | 94 | 234 | 293 | 225 | 248 | 222 |
| 27 | 87 | 239 | 306 | 233 | 256 | 234 |

Myverol is a distilled glyceryl monolinoleate, Tripro is glyceryl tripropionate, Capmul is a mixture of mono- and diglycerides of caprylate and caprate, Mono C-8 is monocaproyl glycerol, and Tribut is glyceryl tributrate.

EXAMPLE 5

PSTG Activity as Measured on the DuPont ACA III:

The samples were mixed as described above in Example 4. The following table shows the data for these PSTG's when analyzed on a DuPont ACA III Analyzer.

TABLE 5

| | | Brands of PSTG | | | |
|---|---|---|---|---|---|
| Time (days) | Control | Myverol | Tripro | Capmul | Mono C-8 | Tribut |
| 0 | 100 | 252 | 269 | 250 | 274 | 251 |
| 2 | 97 | 257 | 297 | 250 | 275 | 253 |
| 5 | 102 | 258 | 321 | 257 | 275 | 253 |
| 9 | 104 | 257 | 326 | 257 | 281 | 257 |

EXAMPLE 6

PSTG Activity as Measured on Ciba Coming's Express 550:

The samples were mixed as described in Example 4 above. The following table shows the data for these PSTG's when analyzed on the Ciba Coming Express 550.

TABLE 6

| | | Brands of PSTG | | | |
|---|---|---|---|---|---|
| Time (days) | Control | Myverol | Tripro | Capmul | Mono C-8 | Tribut |
| 0 | 86 | 247 | 263 | 244 | 271 | 249 |
| 2 | 83 | 246 | 300 | 240 | 272 | 240 |
| 5 | 90 | 261 | 321 | 239 | 272 | 250 |
| 9 | 90 | 246 | 323 | 240 | 267 | 248 |

EXAMPLE 7

PSTG Activity as Measured on Kodak's Ektachem 7000XRC Analyzer:

The samples were mixed as described above in Example 4. The following table shows the data for these PSTG's when analyzed on Kodak's Ektachem 7000XRC Analyzer. Only a single time point is shown here, but serves very well to show that these PSTG's work quite well on this analyzer also.

TABLE 7

| | | Brands of PSTG | | | |
|---|---|---|---|---|---|
| Time (days) | Control | Myverol | Tripro | Capmul | Mono C-8 | Tribut |
| 23 | 91 | 268 | 335 | 258 | 287 | 260 |

EXAMPLE 8

The Use of a PSTG(Capmul) in a Complete Chemistry Control:

Sufficient Capmul MCM (a PSTG) is added to a human serum based complete chemistry control to give a final triglyceride value of about 200 mg/dL when the control is assayed on a DuPont D-380. The chemistry control contains about 50 separate analytes, and shown in the following table are a few representative analytes along with the PSTG acting as most of the triglyceride component. The control material was held at 5° C., and the activity of the various analytes was determined at the time intervals shown.

TABLE 8

| Time (days) | ACP | ALP | Bilirubin | CK | AST | ALT | TRIG |
|---|---|---|---|---|---|---|---|
| 0 | 3.76 | 165 | 7.55 | 251 | 222 | 147 | 212 |
| 1 | 3.86 | 178 | 7.46 | 233 | 214 | 142 | 218 |
| 2 | 3.83 | 181 | 7.28 | 227 | 214 | 143 | 227 |
| 4 | 3.77 | 179 | 7.01 | 231 | 218 | 147 | 233 |
| 6 | 3.74 | 171 | 6.79 | 232 | 221 | 144 | 217 |
| 9 | 3.71 | 171 | 6.31 | 218 | 215 | 137 | 238 |

The data in this table clearly show the stability of this PSTG in the presence of numerous other components.

Further variations in the development of control materials comprising triglyceride substitutes will become apparent to those with expertise in the relevant art.

EXAMPLE 9

Use of a Control in the Monitoring of a Triglyceride Assay

The chemistry control as described in example 8 was assayed for triglyceride alongside two unknown human serum samples on a DuPont D-380 clinical analyzer. The triglyceride value in this control was assigned a value of 220 plus or minus 10%. All samples were run in triplicate.

TABLE 9

| | Sample value mg/dl |
|---|---|
| Control from example 8 | 211, 221, 217 |
| Patient A | 110, 112, 118 |
| Patient B | 245, 250, 248 |

Since the values obtained on the control were within plus or minus 10% of the assigned value of 220 the clinical chemist would have confidence in the values obtained on patients A and B.

What is claimed is:

1. A process for making a clinical control, calibrator or standard for triglyceride determination, comprising adding, to an aqueous protein solution that is similar to human serum, plasma, urine or spinal fluid, components selected from the group consisting of glyceryl monolineate, glyceryl tripropionate, glyceryl tributyrate, and mixtures of mono- and di-glycerides of caprylate and caprate.

2. In a process for determining triglyceride in a sample which employs a control, calibrator or standard, the improvement comprising the control, calibrator or standard comprises one or more components selected from the group consisting of glycerol monolineate, glycerol tripropionate, glycerol tributyrate, and mixtures of mono- and di-glycerides of caprylate and caprate which are lipase substrates and which are dissolved in an aqueous protein solution selected from the group consisting of serum, plasma and albumin, wherein said control, calibrator or standard remains stable for approximately 3 years when stored unopened and refrigerated and does not contain any surfactant or emulsifier.

3. A process of claim 2 wherein said control, calibrator or standard is a single-component control, calibrator or standard.

4. A process of claim 2 wherein said control, calibrator or standard is a multi-component control, calibrator or standard.

5. A process of claim 2 wherein said control, calibrator or standard maintains its stability for about 2 weeks when opened and refrigerated.

6. A process of claim 2 in which said aqueous protein solution is from animal origin.

7. A process of claim 6 in which said aqueous protein solution is from human origin.

8. A process for making a control, calibrator or standard for triglyceride determination, wherein said improvement comprising making said control, calibrator or standard which comprises one or more components selected from the group consisting of glycerol monolineate, glycerol tripropionate, glycerol tributyrate, and mixtures of mono- and di-glycerides of caprylate and caprate in an acceptable carrier selected from the group consisting of serum, plasma and albumin, wherein said control, calibrator or standard has an effective stability of approximately 3 years when stored unopened and refrigerated and does not contain any surfactant or emulsifier.

9. A process of claim 8 wherein said control, calibrator or standard also maintains its stability for about 2 weeks when opened and refrigerated.

10. A process of claim 8 in which said acceptable carrier is from animal origin.

11. A process of claim 10 in which said acceptable carrier is from human origin.

12. A process of claim 8 wherein said control, calibrator or standard is a single-component control, calibrator or standard.

13. A process of claim 8 wherein said control, calibrator or standard is a multi-component control, calibrator or standard.

14. In a method for determining triglyceride, which method employs a control, calibrator or standard, the improvement comprising the control, calibrator or standard comprises one or more components selected from the group consisting of glycerol monolineate, glycerol tripropionate, glycerol tributyrate, and mixtures of mono- and di-glycerides of caprylate and caprate in an acceptable carrier wherein said control, calibrator or standard (1) has an effective stability of approximately 3 years when stored unopened and refrigerated, (2) maintains stability about to 2 weeks when opened, (3) does not contain any surfactant or emulsifier, (4) has a carrier which is selected from the group consisting of serum, plasma and albumin, and (5) has a carrier from human or other animal origin.

* * * * *